(12) United States Patent
Cross et al.

(10) Patent No.: US 7,696,728 B2
(45) Date of Patent: Apr. 13, 2010

(54) TOOTHBRUSH

(75) Inventors: David Murray Cross, Melbourn (GB); David Richard Stonehouse, Melbourn (GB); Timothy Michael Wood, Melbourn (GB)

(73) Assignee: Glaxo Group Limited, Greenford, Middlesex (GB)

( * ) Notice: Subject to any disclaimer, the term of this patent is extended or adjusted under 35 U.S.C. 154(b) by 18 days.

(21) Appl. No.: 10/577,966

(22) PCT Filed: Nov. 2, 2004

(86) PCT No.: PCT/EP2004/012489

§ 371 (c)(1),
(2), (4) Date: Jul. 27, 2007

(87) PCT Pub. No.: WO2005/043709

PCT Pub. Date: May 12, 2005

(65) Prior Publication Data

US 2007/0273331 A1 Nov. 29, 2007

(30) Foreign Application Priority Data

Nov. 4, 2003 (GB) .................................. 0325735.9
Jan. 22, 2004 (GB) .................................. 0401382.7

(51) Int. Cl.
*H02J 7/00* (2006.01)

(52) U.S. Cl. ...................... 320/166; 320/114; 320/112; 320/115

(58) Field of Classification Search ................. 320/166, 320/167, 114, 115
See application file for complete search history.

(56) References Cited

U.S. PATENT DOCUMENTS

| 3,577,579 | A  |   | 5/1971  | Duve             |         |
|-----------|----|---|---------|------------------|---------|
| 5,561,881 | A  | * | 10/1996 | Klinger et al.   | 15/22.1 |
| 5,727,273 | A  | * | 3/1998  | Pai              | 15/22.1 |
| 6,437,544 | B1 | * | 8/2002  | Yang             | 320/167 |
| 6,798,169 | B2 | * | 9/2004  | Stratmann et al. | 320/114 |

FOREIGN PATENT DOCUMENTS

| DE | 19513539   | 10/1996 |
|----|------------|---------|
| WO | WO 96/09019 | 3/1996 |
| WO | WO 97/08804 | 3/1997 |

OTHER PUBLICATIONS

JP 2000 245072 A, *Patent Abstracts of Japan*, vol. 2000, No. 12 (Jan. 3, 2001).
JP 08 088942 A, *Patent Abstracts of Japan*, vol. 1996, No. 8 (Aug. 30, 1996).

* cited by examiner

*Primary Examiner*—Edward Tso
*Assistant Examiner*—Alexis Boateng
(74) *Attorney, Agent, or Firm*—Nora Stein-Fernandez; Theodore R. Furman (57) ABSTRACT

A combination of an electrically powered toothbrush incorporating an electric power supply which comprises a capacitor, and a charging unit which incorporates one or more replaceable or rechargeable battery cells, enabling recharging of the capacitor without connection to the main electricity supply.

21 Claims, 5 Drawing Sheets

TOOTHBRUSH

This application is a §371 National Phase entry of international application number PCT/EP2004/012489, filed Nov. 2, 2004.

This invention relates to toothbrushes, in particular to electrically powered toothbrushes.

Electrically powered toothbrushes are well known articles. They generally comprise a head which supports a bristle carrier from which bristles (the term "bristle" as used herein encompasses other dental cleaning elements such as plastics material or elastomeric flaps, strips, fingers or lamellae) extend in a bristle direction, the head being connected to (or connectable to in a replaceable head toothbrush) a grip handle. The bristle carrier is moveable to move the bristles in a tooth-cleaning effect, e.g. in a rotary, oscillatory rotary, reciprocal, vibratory, combinations thereof or other direction, and can be driven in this movement by a small electric motor. The motor is generally located in the grip handle and connected to the bristle carrier by a suitable gearbox, transmission or drive train, but electric toothbrushes are known in which the motor is located in the head or in a neck between the head and handle. Motors are well known which can produce rotary, oscillatory rotary, reciprocal, vibratory, combinations thereof or other types of motion.

Such a motor needs an electric power supply and this is normally also located in the handle. Additionally the handle normally includes suitable controls such as an on-off switch, speed control etc. At present there are two main types of power supply. One type is one or more replaceable battery which can be replaced within the handle, typically one or two AA or AAA cells. There are many commercial examples of such toothbrushes. Such replaceable batteries may be non-rechargeable or re-chargeable. Some users of electric toothbrushes dislike the cost and inconvenience of replacing batteries. Moreover commonly used AA cells are quite heavy and bulky, thereby restricting the compactness of a handle containing AA cells.

A second type of power supply is one or more rechargeable battery within the handle which can be recharged by docking the toothbrush with a charging station which is connected with the electric mains. There are many commercial examples of such toothbrushes.

It is also known to use a capacitor as an electric power supply for such a motor. DE-A-195 13 539 discloses a capacitor-powered toothbrush that comprises a charging station with inductive (non-contact) charging of a capacitor. The charging station is powered from the mains supply. JP-A-8088942 discloses a circuit of the same architecture as DE-A-195 13 539 with a mains powered charging station base unit and inductive charging. JP-A-2000245072 discloses a mains powered charging station base unit that appears to charge a capacitor in the charging station. The electrical energy is transferred from the capacitor in the charging station to another capacitor in the handle via electrical contacts, until the voltages on the capacitors are equal.

Toothbrush users normally clean their teeth in the bathroom (the term "bathroom" herein refers to any room where the user normally performs washing, regardless of whether it includes a bath), and there is a prejudice against using devices in the bathroom which need to be connected to the mains because of the risks associated with water and mains electricity. Moreover for this reason many bathrooms are not provided with suitable mains sockets.

It is an object of this invention to provide an electric toothbrush with an improved electric power supply, providing inter alia greater convenience, and improved compactness and weight. Other advantages will be apparent from the following description.

Accordingly this invention provides:

an electrically powered toothbrush comprising a head which supports a bristle carrier, the head being connected to or connectable to a grip handle, the bristle carrier being moveable by an electric motor in the toothbrush to provide a cleaning effect, and incorporating an electric power supply which comprises a rechargeable electricity storage means, said means comprising:

a capacitor capable of containing sufficient electric charge to drive the motor for a tooth cleaning session, in combination with a charging unit which incorporates an electricity supply comprising one or more replaceable or rechargeable battery cell, and having an electrical connection means connectable to a corresponding connection on the toothbrush to enable electrical connection between the rechargeable electricity storage means and the charging station, and with which the toothbrush may be connected.

The invention is based on the finding that one or more modern commercially available capacitor can contain sufficient electric charge to drive the types of electric motor commonly used in electric toothbrushes for a useful period, and can directly replace one, two or more AA or AAA size batteries for this purpose, and in particular that such capacitor(s) can rapidly be charged with sufficient electrical power for a toothbrushing session by connection with one or more replaceable or rechargeable battery cell, e.g. one, two or more AA or AAA size batteries in the charging station, without the need to connect the charging station to the electricity mains during the charging of the capacitor(s).

Generally the capacitor needs to provide electric power sufficient to drive the motor for at least 1 minute, preferably 2 minutes or more, for example up to 3 minutes or more, i.e. in line with dentists' recommendations for tooth brushing session times for adequate dental hygiene. Typically the rotary electric motors commonly used in electric toothbrushes have an 0.3 W drive shaft power rating, with an estimated efficiency of 50%. Consequently the capacitor should be capable of delivering 0.6 W electric power for this time period. Typically such motors can operate on a voltage supply of 1.5-3 volts, i.e. the typical output voltage of one or two (parallel or series connected) AA or AAA batteries, and the capacitor should be capable of delivering such an output voltage. It is found that a capacitor with a capacity of 15-50 Farad, preferably 16-22 Farad is capable of meeting these requirements, typically having a working output voltage of 1-5-3V, typically 2.5+/−0.25V.

Such capacitors are known, sometimes being termed in the art "Supercapacitors", "Ultracapacitors" or "Electrochemical double layer capacitors (EDLC)". They have ca. 2000× the volumetric capacitance of standard aluminium electrolytic capacitors. They combine the high energy density of batteries and the high power of capacitors. Such capacitors generally use high surface area carbon for accumulation of charge as opposed to the low surface area foils used in electrolytic capacitors. Suppliers include Panasonic, Elna, Epcos and Cooper Technologies. For example Cooper Technologies' supercapacitors use aerogel carbon as the active material which offers high surface area and high electrical conductivity.

The capacitor may comprise a single capacitor e.g. of the capacity mentioned above, or two or more capacitors to provide the above-mentioned electrical charge storage capacity in a series or parallel connection, e.g. to the motor.

In addition to the ability to charge the capacitors from one or more batteries without a mains connection during the charging process, other benefits of use of such a capacitor for electric toothbrushes include the following.

Such capacitors can be charged vary rapidly, e.g. in less than 1 minute, some in less than 30 seconds, even less than 15 seconds, compared with the several minutes or hours required by ordinary rechargeable batteries. Typically supercapacitors can be charged for 1000+ charge cycles without detrimental effects or reduced life. Supercapacitors are also light weight (lighter than equivalent dry cells) and low volume. For example capacitors of various capacities have typical outside diameter and length dimensions as below:

| Capacitance (F) | Dimensions (mm) |
| --- | --- |
| 50 | 18 OD × 40 L |
| 33 | 33 OD × 35 L |
| 22 | 16 OD × 35 L |

Supercapacitors have an extremely low internal resistance for high power, low loss charging and discharging.

Moreover capacitors are environmentally friendly, containing no undesirable materials such as cadmium or zinc etc.

A particular advantage of a capacitor is that it need not be made in the typical cylindrical shape of a dry cell. The capacitor normally needs to be in the form of a closed loop, but this need not be cylindrical and so can be e.g. elliptical or "U" shaped in section, or a shorter fatter cylinder than the typical dry cell, or a hollow shell e.g. a tube within which other components of the electric toothbrush may be enclosed. This means that the capacitor can be adapted to the shape of the toothbrush handle, rather than dictating the shape of the toothbrush handle.

Yet another advantage of the use of a capacitor as a source of electric power is that the toothbrush can be arranged to automatically stop when a suitable use time has elapsed, i.e. when the electric charge has been used up. This can act as a signal to the user that a suitable brushing time has elapsed, and can avoid the accidental battery run-down that may occur with a normal electric toothbrush using a dry cell if it is left switched on. A typical toothbrush electric motor driven using a capacitor as described above can for example run at a suitable brushing speed (as common in the art) for ca. 2 minutes then start to slow down with a noticeable change in motor noise.

It is also believed to be novel per se to use certain of the above-described capacitors as an electric power supply for an electrically powered toothbrush.

Therefore in a further aspect this invention provides an electrically powered toothbrush comprising a head which supports a bristle carrier, the head being connected to or connectable to a grip handle, the bristle carrier being moveable by an electric motor in the toothbrush to provide a cleaning effect, and incorporating an electric power supply which comprises a capacitor with a capacity of 15-50 Farad capable of containing sufficient electric charge to drive the motor for a tooth cleaning session.

Preferably the capacitor has a capacity of 16-22 Farad. Typically the capacitor has a working output voltage of 1-5-3V, typically 2.5+/−0.25V. The toothbrush may incorporate two or more capacitors in a series or parallel connection to the motor to provide the mentioned electrical storage capacity.

In an embodiment the charging unit is adapted to apply a voltage $V1$ to the capacitor when the toothbrush is connected to the unit, and to temporarily apply a voltage $V2$ higher than $V1$ to the capacitor.

When such a charging unit applies the voltage $V1$ to the capacitor, the voltage $V1$ being equal to or above the charging input voltage of the capacitor, the capacitor becomes and remains charged. Then shortly before the removing the toothbrush from the unit for use the charging voltage is temporarily increased to $V2$. The benefit of temporarily increasing the charging voltage to $V2$ is as follows. By charging a capacitor with a higher input voltage than its specified normal charging voltage the charged capacitor can deliver more output power, or a required power for a longer period than if charged at a lower voltage. But if such a higher voltage is applied to the capacitor for a sustained period this can damage the capacitor. Therefore with the invention the capacitor can be charged and maintained charged by the lower charging voltage $V1$, and the higher "boost" voltage $V2$ may only be applied to the capacitor shortly, e.g. immediately, before use to achieve the benefit of the higher voltage charging but with reduced risk of damage.

With the capacitors of the type discussed herein a suitable $V1$ is 2-3 volts, e.g. the nominal 2.4 volts delivered by two NiCd rechargeable cells connected in series, or the nominal 3 volts delivered by two typical AA or AAA replaceable cells in series. A suitable $V2$ is 3-4 volts e.g. the nominal 3.6 volts delivered by two NiCd rechargeable cells connected in series, or the nominal 4.5 volts delivered by three typical AA or AAA replaceable cells in series. Such capacitors may have such a $V1$ applied to them constantly to maintain them charged, and may have such the voltage $V2$ applied for 10 seconds or less, e.g. 5 seconds or less immediately prior to use.

Suitably therefore the charging unit may incorporate a suitable number, e.g. 2-4 dry cells each of nominally 1.5V output, e.g. replaceable cells, such as AA or AAA batteries. The charging unit may be constructed to connect the capacitor to a first number of replaceable cells to apply $V1$, then to a second, larger, number of replaceable cells to apply $V2$. Typically such a charging unit may comprise a holder incorporating one or more, typically three, such dry cells. The charge characteristics of a capacitor depends upon the source impedance of the supply. Typically a capacitor as described above may be charged by application of a voltage $V1$ by connection to a voltage source of ca. 3.0 V, i.e. two typical dry cells in series. Replaceable alkaline disposable cells can charge a 22F capacitor in about 20 seconds by application of such a $V1$, and keeping such a voltage $V1$ applied to the capacitor can keep the capacitor charged. Shortly prior to use a voltage $V2$ may be applied by connection to a voltage source of ca. 4.5 V, i.e. three typical dry cells.

The charging unit may alternatively incorporate one or more rechargeable cell. Rechargeable NiCd cells are preferred in the charging station as they present the lowest source impedance, can be replaced or trickle charged from a mains supply, and can re-charge a 22F capacitor in about 10 seconds. The charging unit may be constructed to connect the capacitor to a first number of rechargeable cells to apply $V1$, then to a second, larger, number of rechargeable cells to apply $V2$. Suitably therefore the charging unit may incorporate a suitable number, e.g. 2-4 rechargeable NiCd cells, typically each of nominally 1.2-1.3 V output, and means to connect such battery(ies) to the electricity mains for charging in a generally known manner. Such a charging unit may for example have its battery(ies) charged by connection to a mains supply outside the bathroom, then be disconnected from the mains supply and transferred to the bathroom for use, to be re-charged when the charge in the battery(ies) is exhausted. Consequently there is no need for an electricity mains supply in the bathroom.

Typically each such rechargeable cell such as a NiCd cell is capable of delivering a voltage of nominally ca. 1.2-1.3 V. Therefore a capacitor as described above may be charged by application of a voltage V1 by connection to a voltage source of ca. 2.5 V, e.g. two typical rechargeable cells in series. Keeping such a voltage V1 applied to the capacitor can keep the capacitor charged. Shortly prior to use a voltage V2 may be applied by connection to a voltage source of ca. 3.6 V, i.e. three typical rechargeable cells.

The charging unit may be constructed so that sufficient such cells, e.g. two in series, are connected to the capacitor to apply a V1 of ca. 2.4-3.2V, and more e.g. these two plus a third, may then be connected via suitable switching to the capacitor to apply a V2 of ca. 3.6-4.8V. These delivery voltages are stated for new or fully charged cells.

The circuitry of the charging unit or toothbrush may include a resistor in series with the above-mentioned replaceable or rechargeable cells when they deliver V1 to reduce current and to charge the capacitor slowly.

Alternatively, to avoid the use of battery cells the use of which may in time fall foul of antipollution legislation such as the proposed EU WEEE Directive, the charging unit may be constructed to be connected to the electricity mains so as to derive charging and boost voltages V1 and V2 from the mains supply. Such a charging unit may comprise a suitable plug, connection lead, transformer, with switching and circuitry etc. to allow a suitable V1 and V2 to be applied.

Typically to enable the user to apply the voltage V2 for only a short time the charging unit may incorporate a biased switch which is operated by the user against the bias to apply the voltage V2, then when the user ceases to operate the switch the bias disconnects the voltage V2 and re-applies the voltage V1.

The toothbrush may include circuitry to slowly discharge the capacitor if it is left charged at V2 and not used for a predefined period, thereby reducing risk of damage to the capacitor. For example such circuitry may comprise a resistor to ensure slow discharge at low current and a diode e.g. a Zener diode so that discharge only occurs if the discharge voltage of the capacitor is above a set voltage e.g. the nominally 2.5V output voltage of the capacitor mentioned above.

In fact such a discharge circuit is believed to be novel per se when incorporated into an electric toothbrush powered by a capacitor. Therefore according to a further aspect of this invention an electrically powered toothbrush is provided comprising a head which supports a bristle carrier, the head being connected to or connectable to a grip handle, the toothbrush incorporating an electric motor to move the bristle carrier to provide a cleaning effect, and incorporating an electric power supply which comprises a capacitor capable of containing sufficient electric charge to drive the motor for a tooth cleaning session, which includes means to discharge the capacitor if it is charged above a defined voltage. Such circuitry preferably discharges the capacitor if it is left charged above its normal charging voltage and not used.

Suitably the toothbrush can be docked with the charging unit to achieve connection. Preferably the electrical connection means comprise low impedance contacts to deliver the high current charge pulse that occurs during the charging process, metal-to-metal contacts being suitable. For example the toothbrush may have electrical charging contacts on its outer surface which make contact with the connections when the toothbrush is docked with the unit. Preferably such electrical charging contacts on the toothbrush are shielded e.g. recessed to prevent accidental discharge of the charged capacitor.

The toothbrush may also incorporate means to disconnect one or more of the charging contacts from the capacitor when the toothbrush is removed from the charging unit for use. For example such means may comprise a reed switch biased into a state in which a contact is disconnected from the capacitor, and a magnet incorporated into the charging unit to urge the reed switch into a state in which the contact is connected from the capacitor when the toothbrush is connected to the unit.

In fact such means is believed to be novel per se when incorporated into an electric toothbrush having charging contacts. Therefore according to a further aspect of this invention an electrically powered toothbrush is provided comprising a head which supports a bristle carrier, the head being connected to or connectable to a grip handle, the toothbrush incorporating an electric motor to move the bristle carrier to provide a cleaning effect, and incorporating an electric power supply, having charging contacts to facilitate connection of the power supply to a charging unit, and incorporating means to disconnect one or more of the charging contacts from the power supply when the toothbrush is removed from the charging unit.

Other rapid-charging electrical charge storage devices are also known which may be rapidly charged with sufficient electrical power for a toothbrushing session by connection with one or more replaceable or rechargeable battery cell.

Consequently in a further aspect this invention provides:

an electrically powered toothbrush comprising a head which supports a bristle carrier, the head being connected to or connectable to a grip handle, the bristle carrier being moveable by an electric motor in the toothbrush to provide a cleaning effect, and incorporating an electric power supply which comprises a rechargeable electricity storage means capable of being charged with sufficient electric charge to drive the motor for one tooth cleaning session during a charging period of five minutes or less, in combination with a charging unit which incorporates an electricity supply comprising one or more replaceable or rechargeable battery cell, and having an electrical connection means connectable to a corresponding connection on the toothbrush to enable electrical connection between the rechargeable electricity storage means and the charging station, and with which the toothbrush may be connected.

Such a rechargeable electricity storage means is preferably made small and light, enabling an electric toothbrush which is compact and which can be rapidly charged.

Preferably such a rechargeable electricity storage means is capable of being charged with sufficient electric charge to drive the motor for one tooth cleaning session during a charging period of three minutes or less, more preferably two minutes or less, most preferably one minute or less.

It has been found that certain commercially available rechargeable batteries can be charged from one or more other battery cell during the above-mentioned charging period with sufficient electricity to run motors of the above-described types for the typical toothbrushing session times mentioned above, and can be used as the rechargeable electricity storage means. Such rechargeable batteries may be fast charged using a constant current/constant voltage characteristic. NiCd rechargeable batteries have the lowest internal resistance and can recharge at high current equivalent to 3× the cell capacity. Some charge times to re-charge a range of NiCd batteries for a single toothbrushing session are listed below:

| Type | Size | Capacity (mAh) | No. of uses* | charge time for one use (sec)** |
|---|---|---|---|---|
| GP100AAS | AA | 1000 | 60 | 22 |
| GP50AAK | 2/3AA | 500 | 30 | 44 |
| GP18AK | 1/3AA | 180 | 11 | 123 |
| GP30AAAK | AAA | 300 | 18 | 74 |

*Based on a single use of 0.6 W for 2 minutes.
**Assuming a constant 3 C current charge from the discharged state. Partial/rapid charging may accelerate the "memory" effect.

Therefore the rechargeable electricity storage means may comprise one or more NiCd rechargeable battery cell, which as shown above may be rapidly charged by connection to one or more battery cell. Two or more such NiCd battery cells may be connected in series or parallel. NiCd batteries have environmental disposal problems, hence capacitors are preferred to NiCd batteries.

The capacitor and rechargeable electricity storage means of the toothbrushes of this invention may be conveniently initially charged and subsequently re-charged by connection with the charging unit with which it may be connected.

By using such a capacitor an electric toothbrush can be made which is capable of being charged with sufficient electrical power to operate for one or more toothbrushing sessions by means of connection to a charging station incorporating typically 1-4 dry cells. Using capacitors of the above described types the toothbrush may be recharged from ca. three replaceable or rechargeable (e.g. NiCd) dry cells in ca. 10-20 seconds with sufficient electrical power for at least one toothbrushing session, in some cases e.g. with optimised efficient motors, drive train etc, for two or more toothbrushing sessions.

The charging unit may incorporate 1-4 dry cells each of nominally 1.5V output, e.g. household batteries, such as AA or AAA batteries. Typically such a charging unit may comprise a holder incorporating one or more, typically three, such dry cells. The charge characteristics of a capacitor depends upon the source impedance of the supply, but typically a capacitor as described above may be charged by connection to a voltage source of 3.6 V, i.e. 3 typical dry cells (i.e. nominally 4.5V) just prior to use. Such dry cells may themselves be replaceable but non-rechargeable, or may be rechargeable.

Replaceable alkaline disposable cells can re-charge a 22F capacitor in about 20 seconds.

The charging unit may incorporate one or more rechargeable battery. Rechargeable NiCd batteries are preferred in the charging station as they present the lowest source impedance, can be replaced or trickle charged from the mains supply, and can re-charge a 22F capacitor in about 10 seconds. Therefore the charging unit may incorporate one or more (typically three) such battery cell(s) and means to connect such battery (ies) to the electricity mains for charging in a generally known manner. Such a charging unit may for example have its battery(ies) charged by connection to a mains supply outside the bathroom, then be disconnected from the mains supply and transferred to the bathroom for use, to be re-charged when the charge in the battery(ies) is exhausted. It is found that ca. 3 AA batteries are sufficient to repeatedly charge such a capacitor for a period of a month or more, even three months or more, when the electric toothbrush is used twice a day for typical toothbrushing sessions.

A charging unit, provided for a toothbrush as described above, comprises a further aspect of this invention.

Suitably the toothbrush can be docked with the unit to achieve such a connection. Preferably the electrical connection means comprise low impedance contacts to deliver the high current charge pulse that occurs during the charging process, metal-to-metal contacts being suitable. For example the toothbrush may have electrical contacts on its outer surface which make contact with the connections when the toothbrush is docked with the unit. Preferably such electrical contacts on the toothbrush are shielded e.g. recessed to prevent accidental discharge of the charged capacitor by contact with a short circuiting conductor.

Such a charging unit, provided for a toothbrush as described above, comprises a further aspect of this invention.

The head, bristle carrier, overall construction of the handle, motor, controls e.g. on-off switch etc. of the toothbrush and its grip handle may be otherwise conventional.

Some suitable electric toothbrush motors are listed below:

| Manufacturer | Motor | Size (mm) | Reduction Gear ratio | Speed (rpm) | Efficiency (%) |
|---|---|---|---|---|---|
| Johnson | Standard | 20 × 32 | 1:1 | 3500 | 60 |
| Mabuchi | FF-M20VA | 10 × 16.7 | 3:1 | 3000 | 42 |
| Mabuchi | RF-M20VA | 10.1 × 27 | 4:1 | 3500 | 55 |
| Sanyo | TG-1001 | 10 × 17 | 3:1 | 3500 | 50 |
| Sanyo | TG-1201 | 12 × 16 | 3:1 | 3500 | 60 |
| Sanyo | 10L-M-03-150 | 10 × 25 | 4:1 | 3500 | 53 |
| Namiki | SLC10-1806 | 10 × 18.1 | 2:1 | 3500 | 50 |

Typically a rotary or oscillatory rotary motion toothbrush head experiences a load of 200-700 g during use, and it is found that the rotary motors listed may be driven using the capacitor electric power supply or rechargeable electricity storage means of the invention, the Sanyo TG-1001 being a particularly low cost compact motor capable of powering a typical electric toothbrush drive train.

It has been found that a capacitor can be connected directly to the electric motor in a simple replacement for the one or more AA or AAA battery with which the electric toothbrush is normally provided for use. However for some applications it may be advantageous to use known power management circuitry, e.g. on a "chip" to control the power flow from the capacitor to the motor, e.g. a voltage regulator or current limiter to maintain constant speed as the capacitor discharges. Suitable circuitry is apparent to those skilled in the art, or for example as disclosed in DE -A-195 13 539, JP-A-8088942 and JP-A-2000245072 above-mentioned. However it has been found that the toothbrush can function effectively without such circuitry when capacitors of the above-described type are used, e.g. with the capacitor connected directly to the motor with optionally only an on-off switch or circuit breaker between the capacitor and the motor.

The motor may be coupled to the bristle carrier by any conventional transmission means, and may cause the bristle carrier to move in any of the conventional motions of electrically powered toothbrushes. Such a transmission means may cause the bristle carrier to move in rotary or oscillatory rotary motion, and many transmission means are known to do this. Alternatively the transmission means may cause the bristle carrier to move in a so called "Bass" motion. In this latter motion the bristle carrier moves reciprocally along a reciprocation axis, and simultaneously performs oscillatory rotation about the reciprocation axis as a rotation axis. Suitable transmission means to achieve such Bass motion are for example disclosed in WO-A-96/09019 and U.S. Pat. No. 3,577,579.

The invention will now be described by way of example only with reference to the accompanying drawings.

Figure 1:
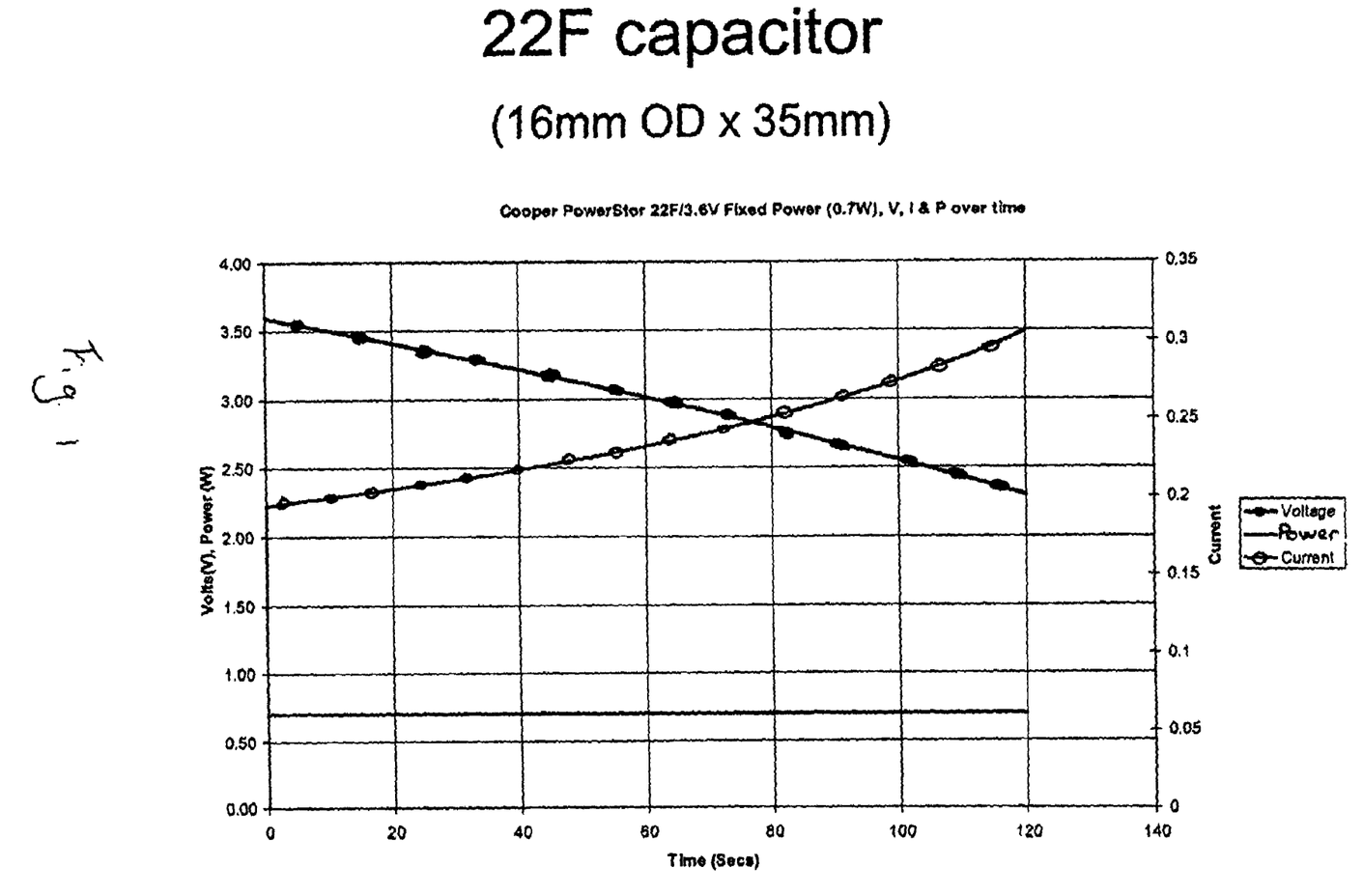
FIGS. 1 and 2 show discharge characteristics for two capacitors.

Referring to FIG. 1 the discharge characteristics of a 22F capacitor, viz. a Cooper PowerStor 22F/3.6V at fixed power (constant 0.7W load), voltage, current and power over time being shown. This capacitor had a size 16 mm OD×35 mm long.

Figure 2:
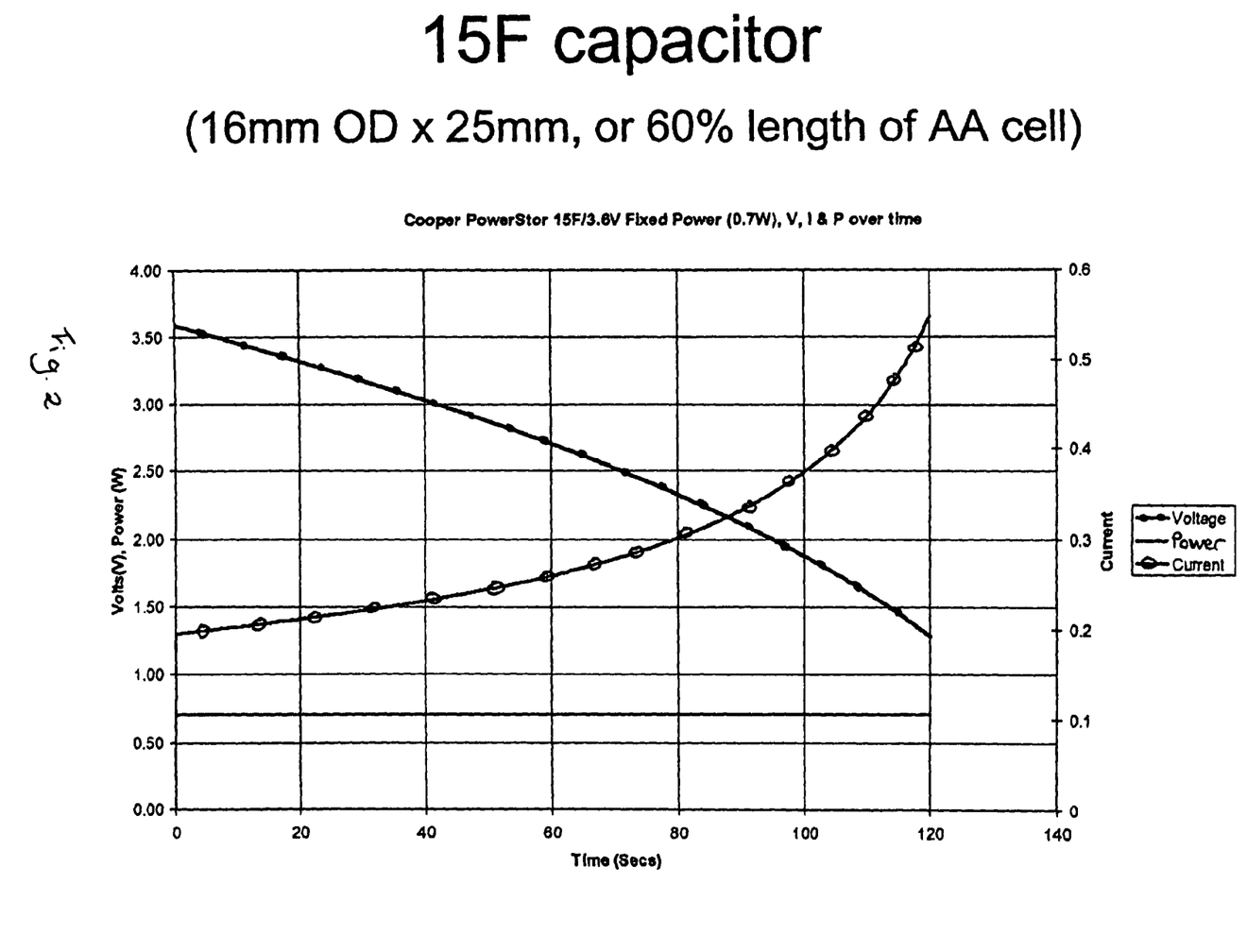

Referring to FIG. 2 the discharge characteristics of a 15F capacitor, viz. a Cooper PowerStor 15F/3.6V at fixed power (constant 0.7W load), voltage, current and power over time being shown. This capacitor had a size 16 mm OD×25 mm long, i.e. 60% of the length of an AA cell.

In both cases the capacitors were initially charged to 3.6V. A known voltage regulation circuit was used, and 85% efficiency was assumed.

In both FIG. 1 and FIG. 2 it is seen that constant power is delivered over a period of at least 100 seconds, corresponding to a typical toothbrushing session.

In an experiment a typical commercially available Dr BEST (GlaxoSmithKline Consumer Healthcare GmbH & Co. KG) electric toothbrush was taken. This is normally powered by two series connected AA batteries, e.g. "Energizer"™ batteries. These powered a rotary motor which in turn drove an oscillatory rotary bristle carrier in the head. Without any other modification the two batteries were removed and replaced by a Cooper PowerStor Aerogel 33F/3.6V capacitor, with the connections of the capacitor connected to the contacts of the battery compartment of the toothbrush.

With the toothbrush switched off the connections of the capacitor were connected for a period of 20 seconds to three AA batteries arranged in series (i.e. nominally ca. 4.5V output). The AA batteries were disconnected from the capacitor and the toothbrush was switched on.

It was found that the toothbrush as powered by the charged up capacitor ran at a comparable speed and delivered comparable torque to the speed and torque formerly achieved when it was powered by the two series connected AA batteries with which it had originally been supplied, for a period of at least two minutes.

Figure 3:
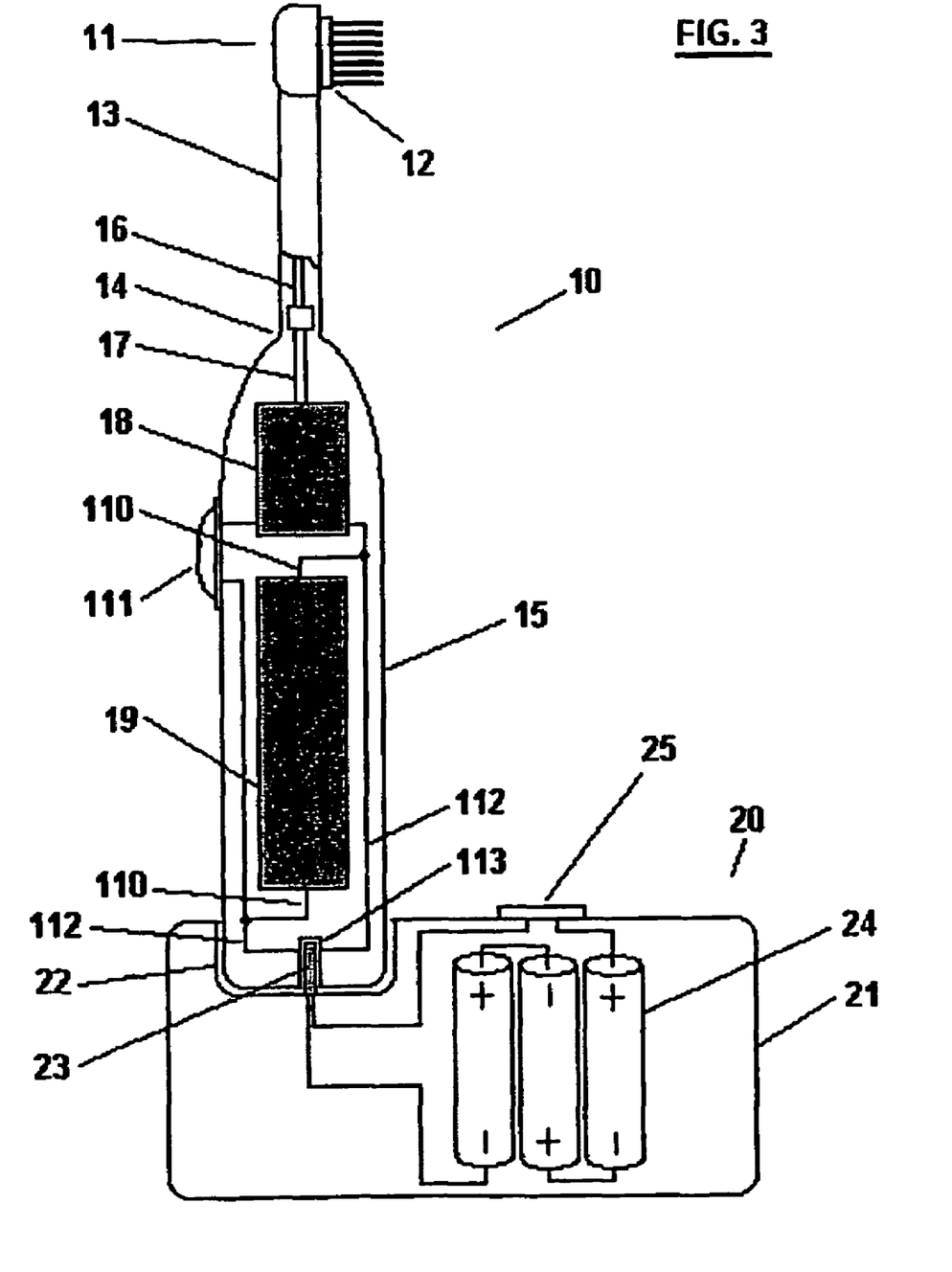
FIG. 3 shows schematically an electric toothbrush of this invention.

Referring to FIG. 3 a typical construction of the electric toothbrush 10 and a recharging unit 20 is shown.

The electric toothbrush 10 is based upon a typical off the shelf replaceable battery-powered toothbrush such as the AQUAFRESH POWERCLEAN. Toothbrush 10 comprises a head 11 which supports a bristle carrier 12 mounted for oscillatory rotary motion in a known manner. The head is integrally formed into tubular neck 13 which is replaceably connectable at end 14 to the grip handle 15. The neck 13 encloses a drive shaft 16. When the neck 13 is connected to handle 15 the drive shaft 16 connects with the output shaft 17 of rotary motor 18, being a typical 0.6W output motor driven by a 3 volt electricity supply, so that the motor 18 can directly drive the shaft 16. In place of the two AA replaceable batteries with which the toothbrush is normally powered there is a PowerStor 33F capacitor 19, which is found to fit easily into the battery compartment in the handle 15. The connections 110 of the capacitor 19 were connected to the positive and negative terminal connections (not shown) of the battery compartment and consequently to motor 18 via the on-off switch 111. The connections 110 are also parallel connected by connectors 112 to metal re-charging contacts of a jack socket 113 fixed in the end of handle 15.

To charge the capacitor 19, with the on-off switch 110 in the "off" configuration to disconnect motor 18 from capacitor 19 the handle 15 is docked with the charging unit 20. Unit 20 comprises a plastics material enclosure 21, which has a cavity 22 to receive the end of the handle 15. Within cavity 22 is situated a corresponding jack plug 23 which when the handle 15 is received in cavity 22 make electrical contact with the contacts of socket 113. Other types of connector may be used to connect the connections 110 of capacitor 19 to the charging unit 20, e.g. metal contacts in the sides of the handle 15.

Unit 20 encloses three serially connected AA batteries 24 e.g. "Duracel" AA cells which are serially connected to the contacts of jack plug 23. Enclosure 21 can be opened to install and replace batteries 24.

When the handle 15 is docked in this way the capacitor receives sufficient charge in ca. 20 seconds via the connection of plug 23 and socket 113 to run the motor 18 for at least 2 minutes. After the capacitor 19 is charged the handle is removed from cavity 22 and the on-off switch 110 may be operated to connect the motor 18 to capacitor 19 to drive the bristle carrier 12 so that the toothbrush 10 can be used. After use the on-off switch 111 is returned to the off setting (alternatively automatic means may be provided to switch the motor off after a suitable time period or when the output of electric power from capacitor 19 drops below a pre-set level), and the toothbrush 10 is returned to the unit 20 so that the plug 113 and socket 112 connect and the capacitor is re-charged for next use.

The unit 20 may also include auxiliary electrical features 25 such as a battery 24 level indicator, or an indicator to show that charging is complete. Alternatively the toothbrush 10 may incorporate such features (not shown).

In an alternative construction the three battery cells 24 may be replaced by three or a different number of rechargeable battery cells such as NiCd battery cells, and the unit 20 may then also incorporate a charging system (not shown) of generally known type to enable the unit to be connected to the electricity mains supply via a suitable transformer (not shown) and suitable conventional circuitry (not shown) to thereby charge rechargeable batteries 24. In such a construction the rechargeable batteries 24 may be charged at a convenient mains socket outside of the bathroom, and when charged (e.g. as indicated by an indicator 25) the unit 20 may be disconnected from the mains and the unit 20 returned to the bathroom. In this state the unit 20 presents no dangers to a user should it accidentally become wet or fall into water in the bath.

In an alternative construction the on-off switch 110 may be omitted and respective electrical contacts, e.g. the socket 113 and plug 23 respectively in the handle 15 and unit 20 may be kept apart, e.g. by a spring bias when the handle is docked in cavity 22. With the handle 15 in cavity 22 the handle 15 may be moved e.g. against the spring bias to bring the contacts together. This causes the batteries 24 to charge the capacitor 19, but simultaneously the capacitor 19 starts supplying electrical power to the motor 18 which starts running. However the capacitor 19 charges up at such a fast rate relative to the power drain through motor 18 that charging of the capacitor 19 still takes place in seconds, e.g. less than 30 seconds. The toothbrush 10 can then be un-docked from unit 20 and used, and the motor 18 stops automatically when the charge in capacitor 19 has been drained by motor 18 to a level insufficient to run motor 18. The head 11 of toothbrush 10 may then be washed under a tap and returned to unit 20.

Figure 4:
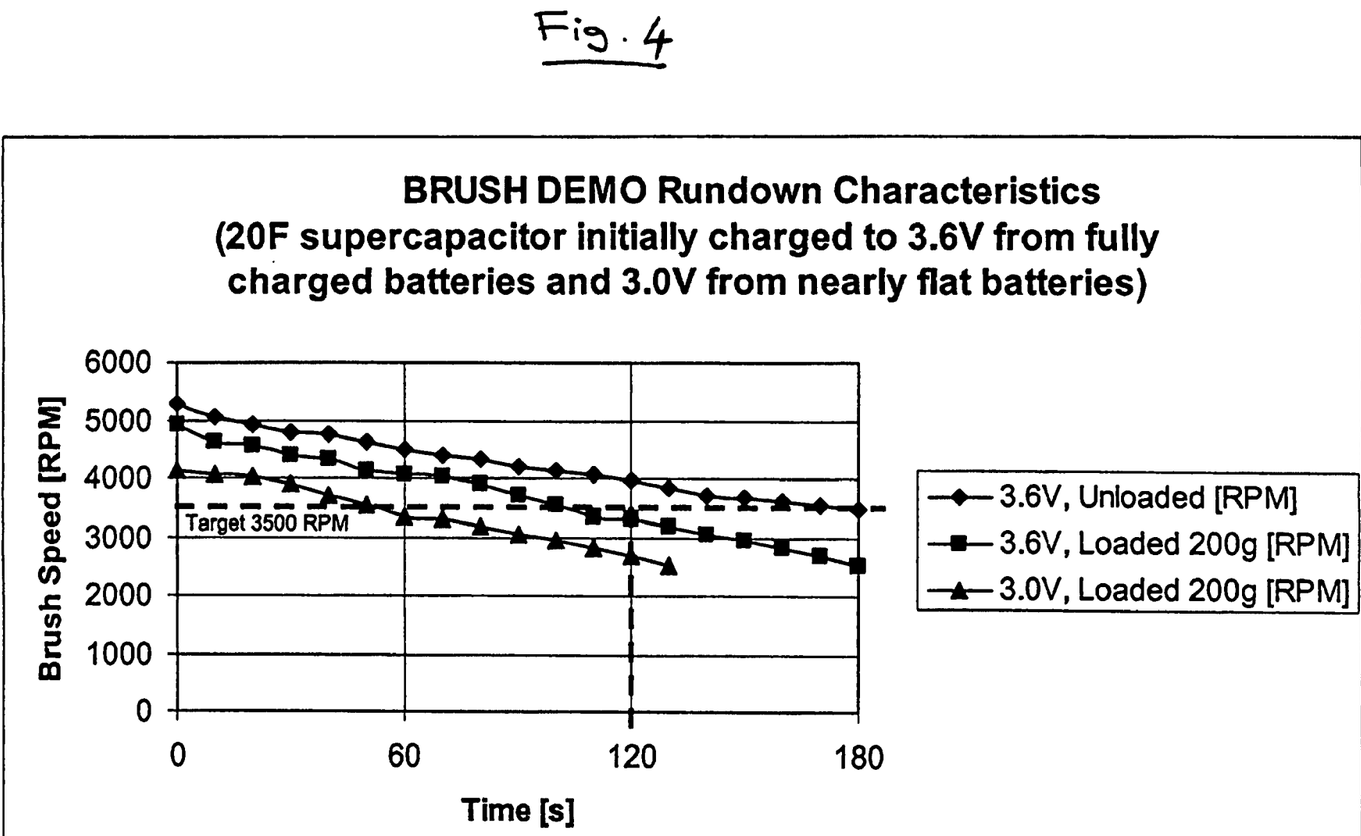
FIG. 4 shows the characteristics of a motor driven by a capacitor.

Referring to FIG. 4 this shows the run down characteristics of an electric toothbrush head driven by a capacitor. A Sanyo "micromotor" TG 1001 was linked to a Maxon 4:1 reduction gearbox and the output shaft of this gearbox was connected directly to the drive shaft of a commercially available replaceable reciprocally-rotary brush head of a commercially available "AQUAFRESH"™ electric toothbrush. The motor was connected directly to a 20F supercapacitor. The three graphs show the run down characteristics following initial charging of the capacitor at 3.6V and running the motor both unloaded and with a 200 g load on the brush head, and initially charging the capacitor at 3.0V then running it with a 200 g load. It is seen that charging at 3.6V enables the motor to run the rotary brush head at a speed above a target 3500 rpm for a longer time than if the capacitor is charged at 3.0V. Loading is defined as pressing the bristle tips of the head against a surface at a pressure of 200 g.

Figure 5:
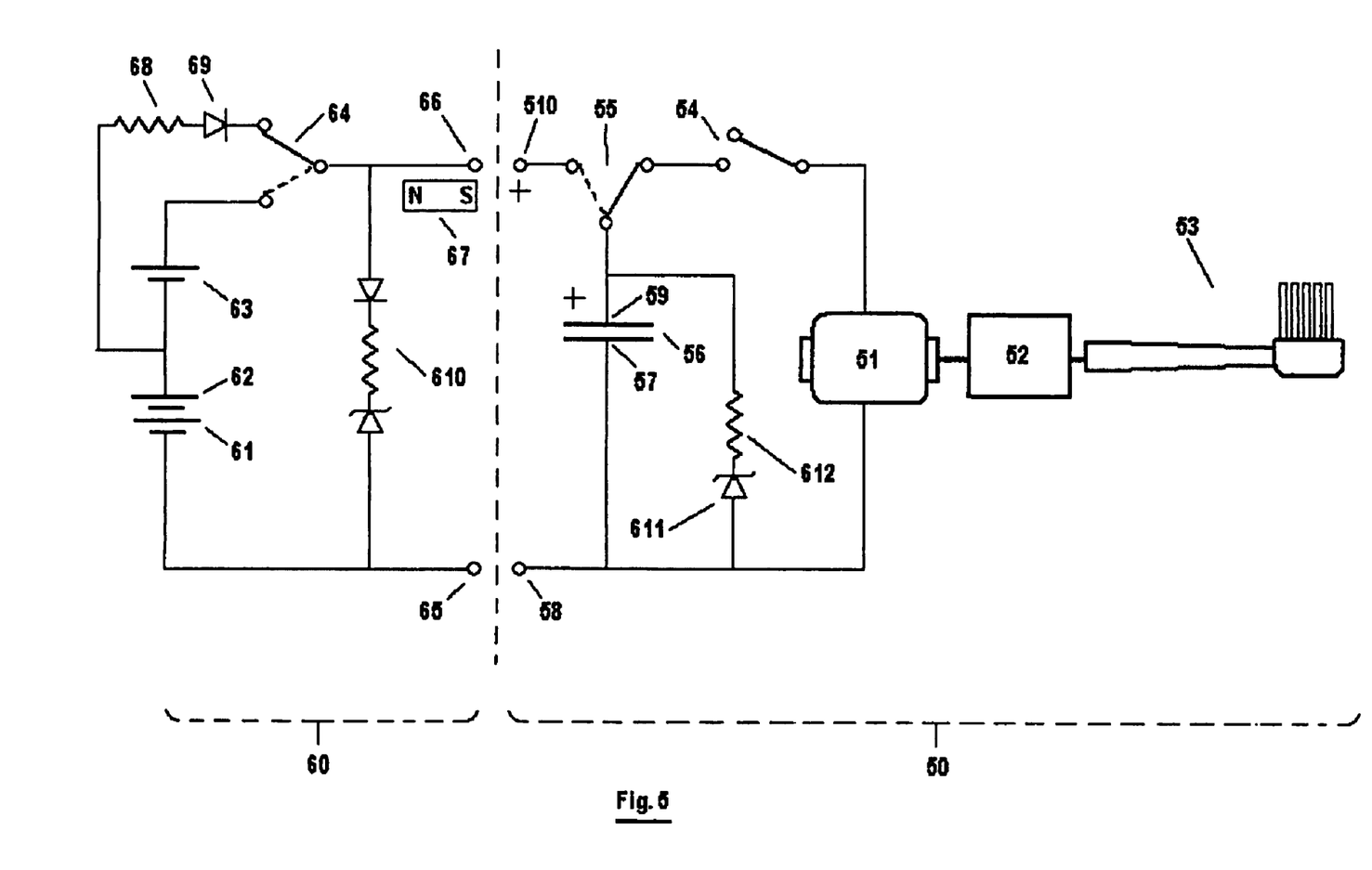
FIG. 5 shows schematically the electric circuitry of an electric toothbrush of this invention.

Referring to FIG. 5 the circuitry of a toothbrush 50 overall is shown schematically. A Sanyo TG-1001 electric motor 51 is linked by a 4:1 Maxon reduction gearbox 52 to a commercial Aquafresh replacement electric toothbrush head 53, though equally well a head 53 having a Bass-type motion could be used. The motor 51 is connected via a manual on-off operating switch 54 and two-way reed switch 55 to a Cooper 20F capacitor 56. One terminal 57 of capacitor 56 is connected to charging contact 58. The other terminal 59 is connected via reed switch 55 to charging contact 510. The reed switch 55 is normally biased into the full line position to connect the capacitor 56 via switch 54 to motor 51.

The circuitry of a charging unit 60 overall is also shown. Unit 60 contains three rechargeable NiCd cells 61,62,63 each with an output voltage of typically 1.2V when fully and freshly charged. Two of these cells 61, 62 connected in series are connected via biased two-way switch 64 to charging contacts 65, 66. Switch 64 is biased so that two of the cells 61,62 are normally connected to contacts 65,66 so as to apply a V1 of ca. 2.4V to contacts 65,66. Switch 64 can be operated by a user e.g. by a push button (not shown) to put it into the dotted line position temporarily to connect all three cells 61,62,63 to contacts 65,66 to apply V2 of 3.6V to the contacts 65,66. With this arrangement the toothbrush 50 may be connected to charging unit 60, thereby connecting contacts 58,510 and 65,66. A magnet 67 is located in the charging unit 60 and when the toothbrush 50 is connected to unit 60, e.g. by the toothbrush being brought into close proximity with the unit 60 e.g. into a socket mounting in unit 60 magnet 67 urges reed switch 55 into the dotted line configuration to connect contacts 58,510 to capacitor 56 and to thereby connect capacitor 56 to cells 61,62 via contacts 65, 66.

The capacitor 56 is thereby charged and maintained charged whilst it remains connected to unit 60. Immediately prior to use switch 64 is operated by the user for e.g. five seconds against its bias to apply ca. 3.6V to capacitor 56. After this the user may release pressure on the operating button (not shown) to return switch 64 to its normal closed line biased position. The toothbrush 50 can then be disconnected from unit 60. This action removes magnet 67 from close proximity to reed switch 55 so that switch 55 moves into its biased dotted line position to connect capacitor 56 to motor 51 via on-off switch 54. Closing on-off switch 54 connects the capacitor 56 to motor 51 to operate toothbrush head 53.

Other features of the circuitry are shown. A resistor 68 limits the current flow from cells 61,62 to capacitor 16 so that cells 61,62 charge capacitor 16 slowly, and diode 69 protects against backflow of current. A "capacitor charged"/"battery health" indicator is provided at 610, and comprises a Zener diode with a nominal 3.5V rating, an LED and a ballast resistor to prevent overcurrent of the LED. When in boost mode, i.e. with the higher voltage being applied to the capacitor 56 the voltage will dip as the capacitor 56 is charged. As the voltage climbs to 3.5V and the brush is ready for use the Zener diode will allow current to flow and light the LED to indicate readiness for use. A resistor 611 in series with a zener diode 612 is set to slowly discharge capacitor 56 if it is charged with a voltage above ca. 3V, and causes capacitor 56 to discharge if it is charged at above 3V by connection to cells 61,62,63 and left in this charged state without being used as described above.

Although illustrated using cells 61,62,63 to apply voltages V1 and V2 via suitable switching it will be apparent to those skilled in the art how the unit 60 may alternatively be constructed such that unit 60 may be connected to the electricity mains supply and V1 and V2 generated using e.g. a transformer and suitable switching.

It will also be apparent to those skilled in the art how unit 60 as illustrated could also be provided with means to charge cells 61,62,63 from the electricity mains.

Resistors 68, 610, and 611 referred to herein have a nominal resistance of 100 ohm but could be in the range 20-1000 ohm.

The invention claimed is:

1. An electrically powered toothbrush comprising a head which supports a bristle carrier, the head being connected to or connectable to a grip handle, the bristle carrier being moveable by an electric motor in the toothbrush to provide a cleaning effect, and incorporating an electric power supply which comprises a capacitor capable of containing sufficient electric charge to drive the motor for a tooth cleaning session, in combination with a charging unit which incorporates an electricity supply having an electrical connection means connectable to a corresponding connection on the toothbrush to enable electrical connection between the capacitor and the charging unit, and with which the toothbrush may be connected, and wherein the charging unit comprises means to apply a charging voltage V1 to the capacitor when the toothbrush is connected to the unit, and means operable by a user of the toothbrush to temporarily apply a charging voltage V2 higher than V1 to the capacitor after application of charging voltage V1 and prior to use of the toothbrush.

2. A combination according to claim 1 wherein the capacitor provides electric power sufficient to drive the motor for a tooth cleaning session of two minutes or more.

3. A combination according to claim 1 wherein the capacitor is capable of delivering 0.6 W electric power for the tooth cleaning session.

4. A combination according to claim 1 wherein the capacitor has a capacity of 15-50 Farad.

5. A combination according to claim 4 wherein the capacitor has a capacity of 16-22 Farad.

6. A combination according to claim 3 wherein the capacitor has a working output voltage of 1-5-3V.

7. A combination according to claim 1 wherein the capacitor is an electrochemical double layer capacitor.

8. A combination according to claim 1 wherein the toothbrush incorporates an electric power supply which comprises a single capacitor.

9. A combination according to claim 1 wherein voltage V1 is equal to or above the charging input voltage of the capacitor.

10. A combination according to claim 1 wherein the capacitor can be charged and maintained charged by the voltage V1.

11. A combination according to claim 1 wherein V1 is 2-3 volts.

12. A combination according to claim 1 wherein V2 is 3-4 volts.

13. A combination according to claim 1 adapted that voltage V2 may be applied for 10 seconds or less.

14. A combination according to claim 1 wherein the charging unit is constructed to connect the capacitor to a first number of replaceable cells to apply V1, then to a second, larger, number of replaceable cells to apply V2.

15. A combination according to claim 1 wherein the charging unit or toothbrush includes a resistor in series with the replaceable or rechargeable cells when they deliver V1.

16. A combination according to claim 1 wherein the charging unit is constructed to be connected to the electricity mains so as to derive charging and boost voltages V1 and V2 from the mains supply.

17. A combination according to claim 1 wherein the charging unit incorporates a biased switch which is operated by the user against the bias to apply the voltage V2, then when the user ceases to operate the switch the bias disconnects the voltage V2.

18. A combination according to claim 1 wherein the toothbrush includes circuitry to discharge the capacitor if it is left charged at V2 and not used.

19. A combination according to claim 1 wherein the motor is connected to the bristle carrier by a transmission mean which causes the bristle carrier to move in a motion in which the bristle carrier moves reciprocally along a reciprocation axis, and simultaneously performs oscillatory rotation about the reciprocation axis as a rotation axis.

20. A charging unit for a combination as claimed in claim 1.

21. A combination according to claim 1 wherein the power supply comprises one or more replaceable or rechargeable battery cell.

* * * * *